United States Patent [19]

Clemens et al.

[11] 4,055,175
[45] Oct. 25, 1977

[54] BLOOD GLUCOSE CONTROL APPARATUS

[75] Inventors: Anton Hubert Clemens, Elkhart; Robert Weston Myers, Mishawaka, both of Ind.

[73] Assignee: Miles Laboratories, Inc., Elkhart, Ind.

[21] Appl. No.: 685,881

[22] Filed: May 7, 1976

[51] Int. Cl.$^2$ ............................................. A61M 5/00
[52] U.S. Cl. ..................................... 128/213; 128/260
[58] Field of Search .................... 128/2 E, 2 R, 2.1 E, 128/2.1 R, 213, 214, 260; 204/195 B; 235/151.3

[56] References Cited

U.S. PATENT DOCUMENTS

| 3,809,871 | 5/1974 | Howard et al. | 235/151.3 |
| 3,837,339 | 9/1974 | Aisenberg et al. | 128/213 |
| 3,857,771 | 12/1974 | Sternberg | 204/195 B |
| 3,923,060 | 12/1975 | Ellinwood, Jr. | 128/260 |

OTHER PUBLICATIONS

Pagurek et al., "Medical & Biological Engineering," vol. 10, No. 6, Nov. 1972, pp. 752-761.

Primary Examiner—William E. Kamm
Attorney, Agent, or Firm—Louis E. Davidson

[57] ABSTRACT

Apparatus is described for controlling blood glucose concentration in a subject by selected infusion of insulin and/or glucose, depending upon the general blood glucose concentration. This apparatus comprises in combination sensor means for measuring the blood glucose concentration and for providing computer input signals based on such measurement, computer means for receiving such input signals and being programmed to provide output signals based upon such input signals and pump means responsive to such computer output signals to supply insulin and/or glucose to such subject at a rate determined by such output signals. The computer derives the output signals in accordance with specific quadratic and biquadratic equations employing certain independently selected values relating to basal blood glucose concentrations and basal insulin and glucose infusion rates at such basal blood glucose concentrations.

4 Claims, 8 Drawing Figures

BLOOD GLUCOSE CONTROL APPARATUS

BACKGROUND OF THE INVENTION

Individuals afflicted with diabetes mellitus experience varying degrees of malfunctioning of the body cells which produce insulin. Insulin is necessary for proper metabolism of glucose in the blood.

The historical treatment of a diabetic condition was to give periodic injections of insulin and to attempt to control the diet so that the injected insulin could handle the carbohydrate intake. This was somewhat unsatisfactory since the insulin injections were not generally timed to concide with carbohydrate intake. Situations were thus created wherein the amount of insulin present was either in excess of or less than that required to handle the specific blood glucose level at any given time. Such a situation is especially severe when the diabetic is under stressed conditions, such as surgery or childbirth for example.

Various systems and apparatus have been proposed to analyze the blood concentration and to infuse insulin or glucose based upon such analysis to better control the blood glucose to within desired ranges. A significant advance in the art is described in Diabetes, Vol. 23, No. 5, pp. 389 –404 (1974). Apparatus is described having a computer which operated an infusion pump to infuse insulin or glucose based upon analytical blood glucose values. The computer derives the output signals for pump operation from algorithms based upon hyperbolic tangentail functions. While this prior art computer control had many advantages, it had the distinct disadvantage that the responses did not always satisfactory provide adequate control. Also, the apparatus provided only limited flexibility in the selection of specific operating conditions for particular individuals whose blood glucose concentrations were being controlled by the apparatus.

There is thus a need for apparatus for improved control of blood glucose concentration and which also enables a higher degree of flexibility in selecting specific operating conditions.

SUMMARY OF THE INVENTION

In accordance with the present invention, apparatus is provided for controlling the concentration of glucose in the blood stream of a patient by controlled infusion of insulin and/or glucose to such subject dependent upon the glucose concentration of such blood stream comprising in combination means for determining serial values of blood glucose concentration and for providing computer input signals corresponding to said serial values; computer means coupled to receive said serial input signals, said computer means being programmed to provide output signals based upon serial input signals; and pump means responsive to said output signals for supplying insulin and/or glucose to said subject at a rate determined by said output signals; said computer being capable of deriving output signals from such serial input signals in accordance with equations selected from the class consisting of quadratic and biquadratic equations, which equations involve as elements thereof independently selected values of basal blood glucose concentrations and of basal insulin and glucose infusion rates at such basal blood glucose concentrations.

DESCRIPTION OF THE INVENTION

Figure 1:
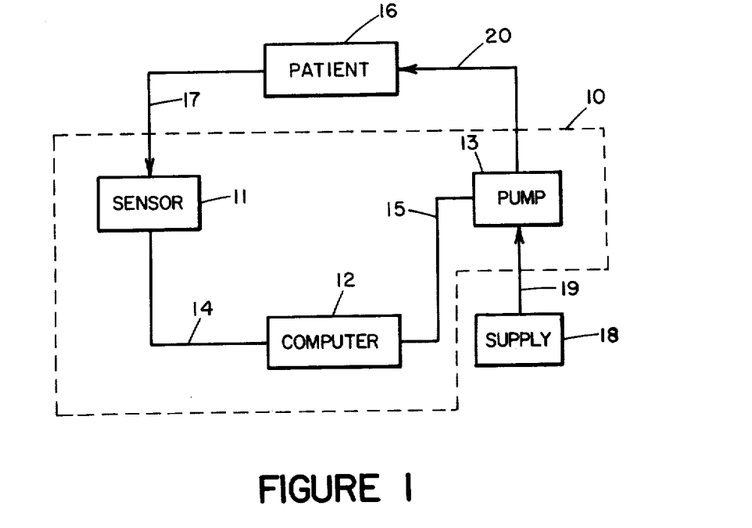
FIG. 1 is a schematic block diagram of the apparatus of the present invention used in coopertion with a diabetic patient.

With reference to FIG. 1, the apparatus 10 of the present invention is schematically shown as comprising the elements of sensor 11, computer 12 and pump 13. Sensor 11 is capable of generating computer input signals which are transmitted to computer 12 over line 14. Computer 12 is capable of generating output signals which are transmitted to pump 13 over line 15. In the operation of this apparatus, blood samples are obtained from patient 16 and are conducted to sensor 11 through conduit 17. Pump 13 is connected to a supply 18 of insulin or glucose through conduit 19 and to the patient 16 through conduit 20. The sensor 11 determines the blood glucose concentrations of blood samples obtained from patient 16 at convenient intervals, such as once each minute, and transmits such serial signals indicative of such blood glucose concentrations to computer 12. The output signals from computer 12 are directly related to the serial blood glucose concentrations measured by sensor 11 and provide instructions to pump 13 to supply adequate amounts of insulin or glucose to bring the blood glucose concentration within the desired range.

The particular novel aspects of the present invention relate to the algorithms or equations which the computer 12 employs to derive the proper output signals based upon the input signals from sensor 11 as well as to the flexibility of operation of such computer.

It has been found through experimentation with blood glucose levels of diabetic patients that improved control over such blood glucose concentration can be achieved through operation in accordance with certain quadratic and biquadratic computer equations.

The apparatus of the present invention is capable of operating in several modes at the choice of the operator.

In a first mode, the insulin is infused to a patient at a rate dependent upon both the particular concentration of glucose in the blood and the rate of change of blood glucose concentration. In a second mode, the insulin is infused at a rate dependent only upon the particular concentration of glucose in the blood. In a third mode, the insulin is infused at a rate dependent only upon the rate of change of blood glucose concentration. In order to overcome a hypoglycemia condition (undesirably low blood glucose concentration) the apparatus also provides infusion of glucose at a rate dependent only upon the particular concentration of blood glucose whenever the blood glucose concentration is below a predetermined value. This latter situation is considered emergency situation to be used primarily when the patient initially is in a hypoglycemis condition. The operation in the first three modes will normally prevent such condition from occurring as a result of infusion of an excess amount of insulin. It could also be used if desired when the operator intends to maintain a "glucose clamping" condition in which the glucose level is maintained at an abnormally high level.

In the above first mode of operation, the computer is capable of deriving output signals from serial input signals in accordance with an equation of the form $$IR = RI \left( \frac{G + GD - BI}{QI} + 1 \right)^4$$

wherein
 IR = calculated insulin infusion rate
 BI = basal glucose concentration
 RI = desired basal insulin infusion rate at BI
 G = measured previous serial blood glucose reading
and BI, RI and QI are preselected values. If the blood glucose concentration is rising, $$GD = LK (K_R A^2 10 + 6A)$$

wherein A is the average change in blood glucose concentration over several previous serial readings and $K_R$ is a preselected value and wherein if the blood glucose concentration is falling, $$GD = (K_F A^2 10 + 6A)$$

wherein A is the same as above and $K_F$ is a preselected value which is different from and less than $K_R$, said GD being substracted from G in the above equation when the blood glucose concentration is falling.

In the above equation IR and RI are expressed in milliunits of insulin per minute of infusion. BI, QI, G, GD and A are expressed in mg. percent of glucose. This can also be expressed as milligrams per deciliter (mg.dl). BI represents a selected basal blood glucose concentration which would be present in a normal patient under resting conditions. RI represents the basal insulin infusion rate normally provided by the body of the normal patient under such conditions. When the apparatus of the present invention is used with a 70 kg. human patient, for example, RI is typically about 9 to 12 milliunits of insulin per min. and BI is about 80 mg. percent glucose. A typical QI is about 85 mg. percent glucose. $K_R$ generally is in the range from 60 to 200 and is typically about 125. $K_F$ generally is in the range from 0 to 100 and is typically about 25. The values for RI, BI, QI, $K_R$ and $K_F$ are selected by the operator depending upon the specific patient involved and upon previous experience.

In the above second mode of operation, the computer is capable of deriving output signals from serial input signals in accordance with an equation of the form $$IR = RI \left( \frac{G - BI}{QI} + 1 \right)^4$$

wherein IR, RI, G, BI and GI are discussed above.

In the above third mode of operation, the computer is capable of deriving output signals from serial input signals in accordance with an equation of the form $$IR = RI \left( \frac{G + GD - BI}{QI} + 1 \right)^4 - RI \left( \frac{G - BI}{QI} + 1 \right)^4$$

wherein IR, RI, G, GD, BI and QI are discussed above.

When the apparatus is employed to infuse glucose, the computer is capable of deriving output signals from serial input signals in accordance with an equation of the form $$DR = RD \left( \frac{BD - G}{QD} + 1 \right)^4$$

wherein
 DR = calculated glucose infusion rate
 BD = basal glucose concentration
 RD = desired basal glucose infusion rate at BD
 G = measured previous serial blood glucose reading
and RD, BD and QD are preselected values.

In the above equation DR and RD are expressed in milligrams per minute of glucose infusion. BD, QD and G are expressed in mg. precent of glucose. BD represents a selected basal blood glucose concentration and RD represents a normal glucose infusion rate to obtain such basal concentration. When the apparatus of the present invention is used with a 70 kg. human patient, for example, RD is about 9 to 11 milligrams of glucose per minute and BD is about 70 mg. percent glucose. A typical QD is about 20 mg. percent glucose.

It has been determined that in order to prevent any undersirable "overshooting" of desired blood glucose concentrations by excess infusion or glucose, the infusion rates for insulin and glucose should have controlled maximum values. A maximum insulin infusion rate of about 600 milliunits per minute and a maximum glucose infusion rate of about 200 milligrams per minute have been found suitable.

Figure 2:
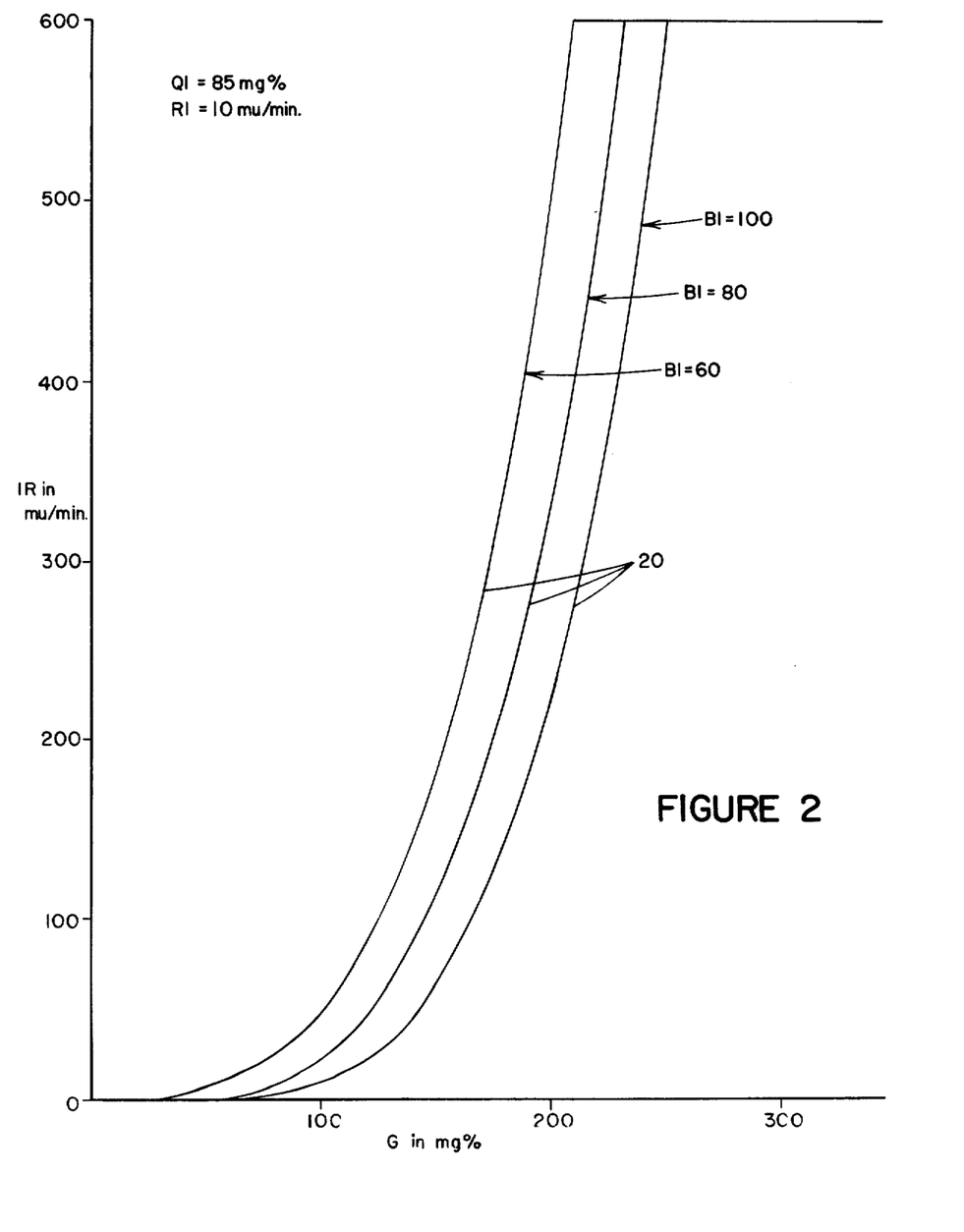
FIG. 2 is a family of curves showing operation of the apparatus of the present invention for insulin infusion vs. blood glucose concentration for several basal glucose concentrations.

Typical operating conditions for computer calculated insulin infusion rates (IR) vs. measured serial blood glucose concentrations (G) for the second mode of operation are shown in FIG. 2. The RI and QI are kept constant at typical values of 10 milliunits per minute and 85 mg. percent, respectively. BI is shown for three typical values of 60, 80 and 100 mg. percent. The calculated IR is then obtained from the appropriate curve 20 depending on the measured blood glucose reading (G) and the appropriate BI selected by the operator. Comparable curves can also be obtained for different values of BI. It is noted that the curves are truncated at a maximum insulin infusion rate of 600 milliunits per minute.

Figure 3:
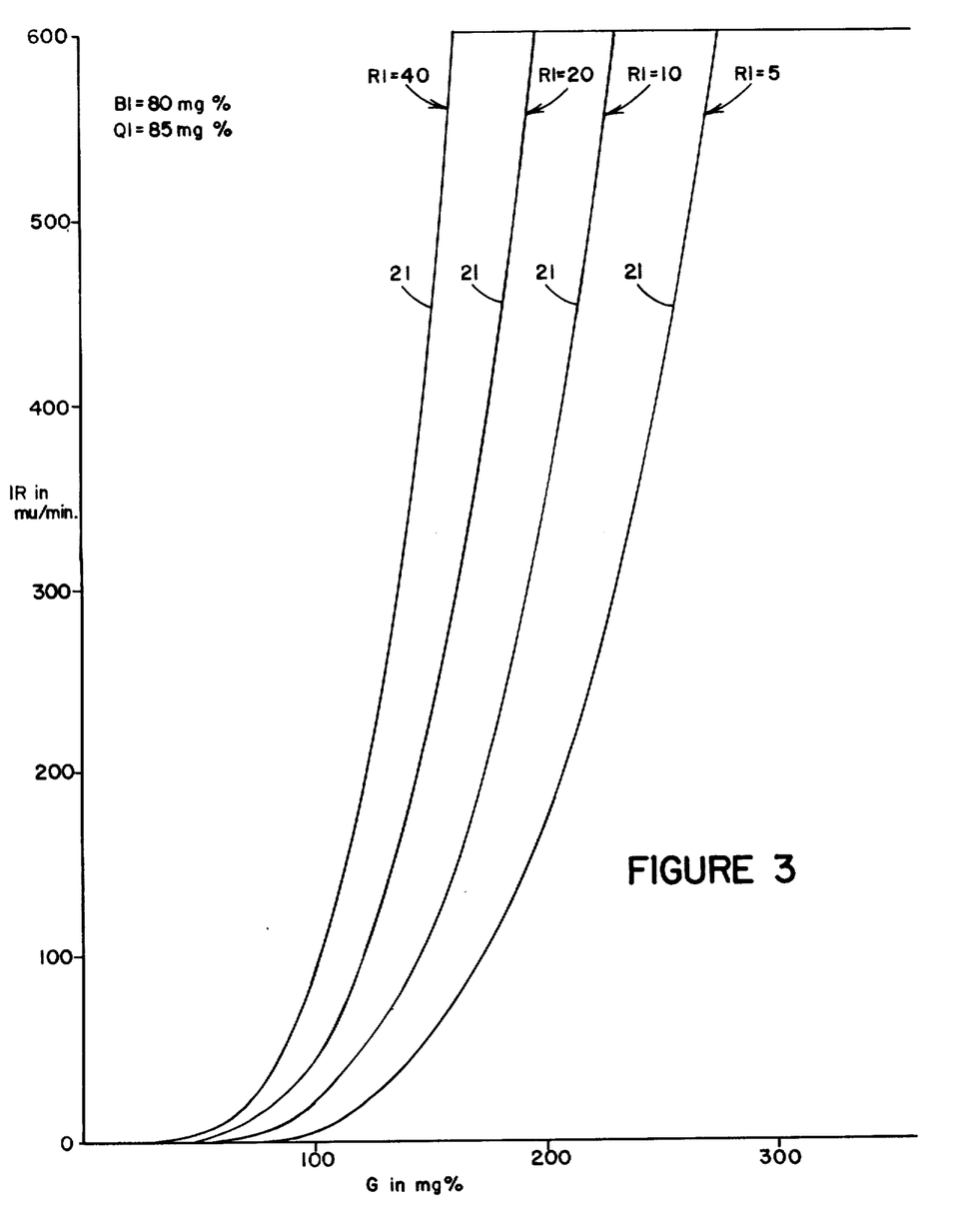
FIG. 3 is a family of curves showing operation of the apparatus of the present invention for insulin infusion vs. blood glucose concentration for several basal insulin infusion rates.

Typical operating conditions for computer calculated insulin infusion rate (IR) vs. measured serial blood glucose concentrations (G) for the second mode of operation are shown in FIG. 3. The BI and QI are kept constant at typical values of 80 and 85 mg. percent, respectively. RI is shown for four typical values of 5, 10, 20 and 40 milliunits of insulin per minute. The calculated IR is then obtained from the appropriate curve 21 depending on the measured blood glucose reading (G) and the appropriate RI selected by the operator. Comparable curves can also be obtained for different values of RI.

Figure 4:
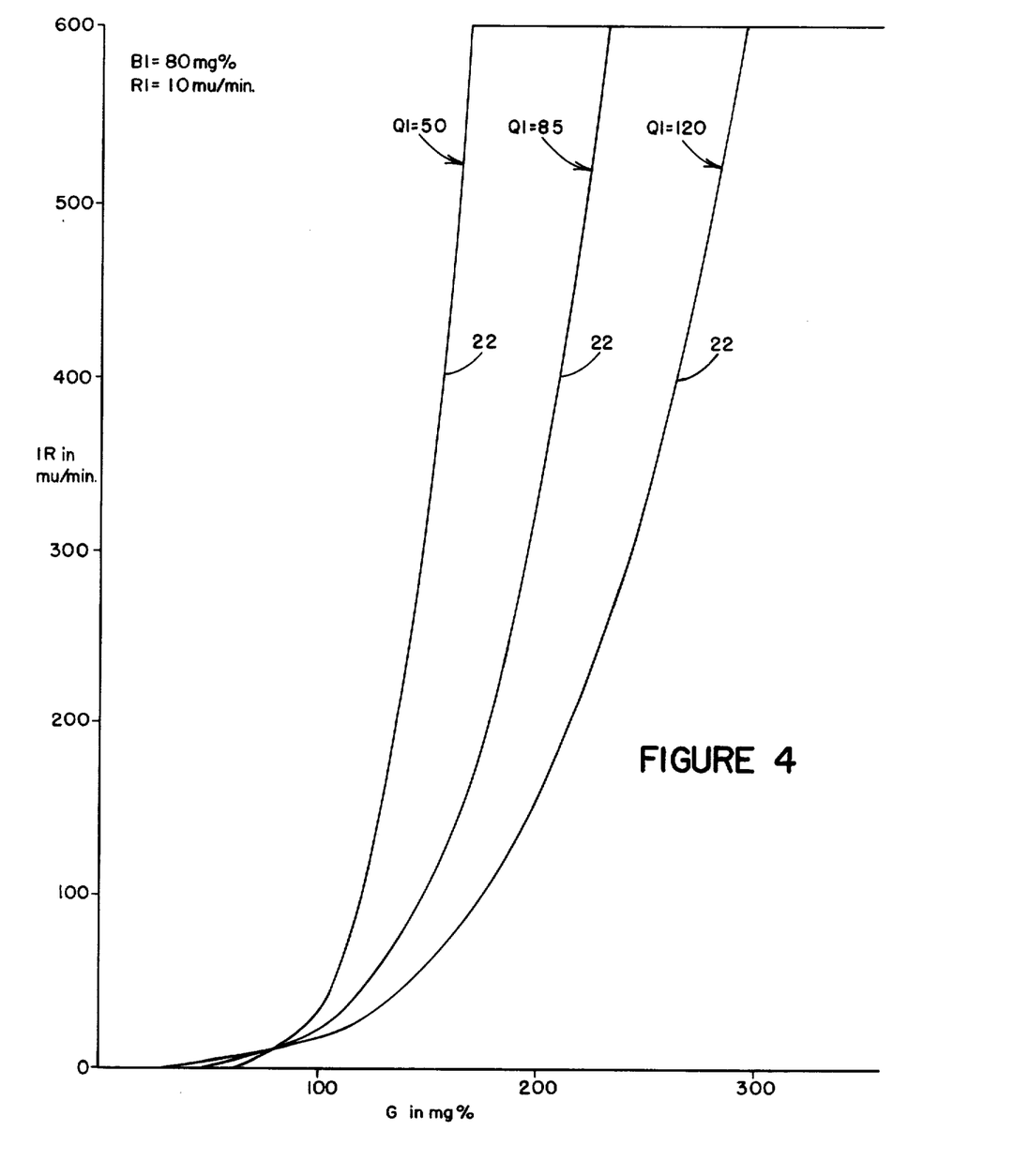
FIG. 4 is a family of curves showing operation of the apparatus of the present invention for insulin infusion vs. blood glucose concentration for several values of QI.

Typical operating conditions for computer calculated insulin infusion rates (IR) vs. measured serial blood glucose concentrations (G) for the second mode of operation are shown in FIG. 4. The BI and RI are kept constant at typical values of 80 mg. percent and 10 milliunits per minute, respectively. QI is shown for three typical values of 50, 85 and 120 mg. percent. The calculated IR is then obtained from the appropriate curve 22 depending on the measured blood glucose reading (G) and the appropriate QI selected by the operator. Comparable curves can also be obtained for different values of QI.

Figure 5:
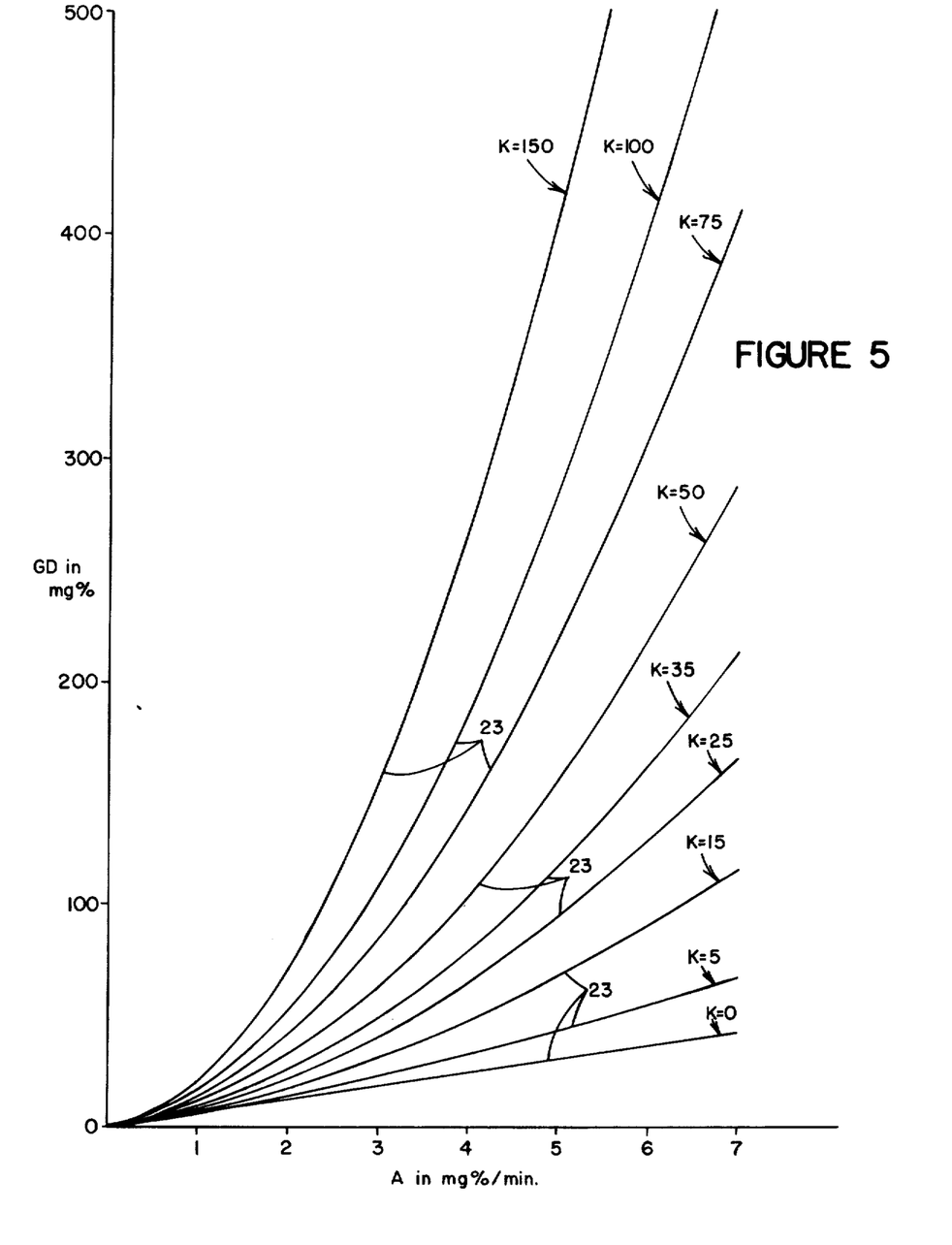
FIG. 5 is a family of curves showing relationships in the operation of the apparatus of the present invention based on rate of change in blood glucose concentration.

Typical operating conditions for computer calculated GD values to be used in the appropriate equations vs. rate of change of blood glucose concentration (A) for the first and third modes of operation are shown in FIG. 5. The effect of variations in K are known by the different curves 23. If the blood glucose concentration is rising, K refers to $K_R$. If the blood glucose concentration is falling, K refers to $K_F$. Comparable curves can also be obtained for different values of K.

In the operation of the apparatus in the various modes for insulin infusion, the portions of the equations relating to (G−BI QI) +1 and (G+GD−BI QI) +1 must have values greater than zero. If either of these portions has values less than zero, the computer will stop all insulin infusion.

Figure 6:
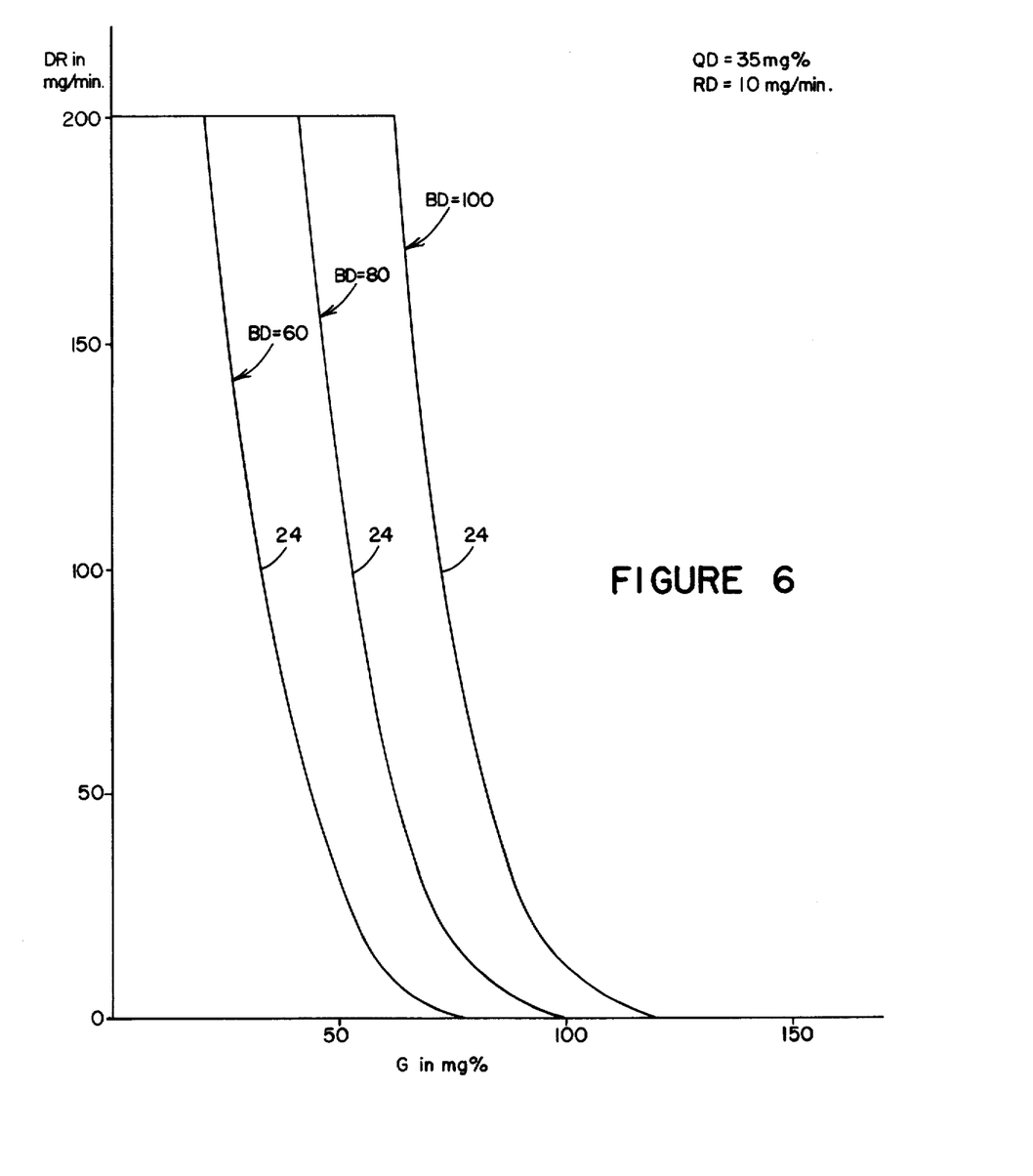
FIG. 6 is a family of curves showing operation of the apparatus of the present invention for glucose infusion vs. blood glucose concentration for several basal glucose concentrations.

In the event that the measured serial blood glucose concentrations drop below about 70 mg. percent, it is desirable to infuse glucose to bring the blood glucose concentration within the desired physiological range. In this case the computer will automatically switch to the glucose infusion mode described above. Glucose infusion according to this mode can also be accomplished at any time at the discretion of the operator irrespective of the specific blood glucose concentration. Typical operating conditions for computer calculated glucose infusion rates (DR) vs. measured serial blood glucose concentrations (G) are shown in FIG. 6. The QD and RD are kept constant at typical values of 35 mg. percent and 10 mg. per min. respectively. BD is shown for three typical values of 60, 80 and 100 mg. percent. The calculated DR is then obtained from the appropriate curve 24 depending on the measured blood glucose reading (G) and the appropriate BD selected by the operator. Comparable curves can also be obtained for different values of BD. It is noted that the curves are truncated at a maximum glucose infusion rate of 200 milligrams per minute.

Figure 7:
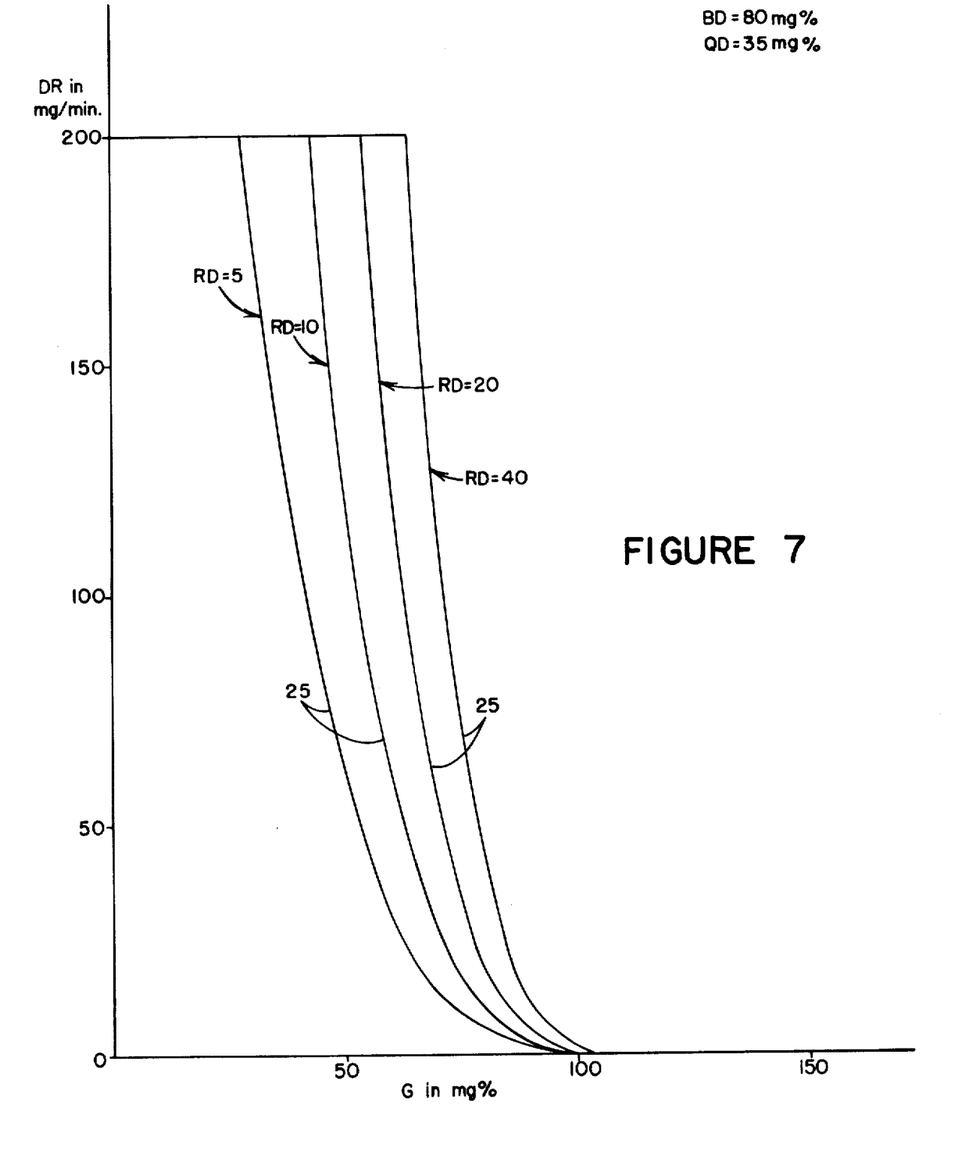
FIG. 7 is a family of curves showing operation of the apparatus of the present invention for glucose infusion vs. blood glucose concentration for several basal glucose infusion rates.

Typical operating conditions for computer calculated glucose infusion rates (DR) vs. measured serial blood glucose concentrations (G) are shown in FIG. 7. The BD and QD are kept constant at typical values of 80 and 35 mg. percent, respectively. RD is shown for four typical values of 5, 10, 20 and 40 mg. per min. The calculated DR is then obtained for the appropriate curve 25 depending on the measured blood glucose reading (G) and the appropriate RD selected by the operator. Comparable curves can also be obtained for different values of RD.

Figure 8:
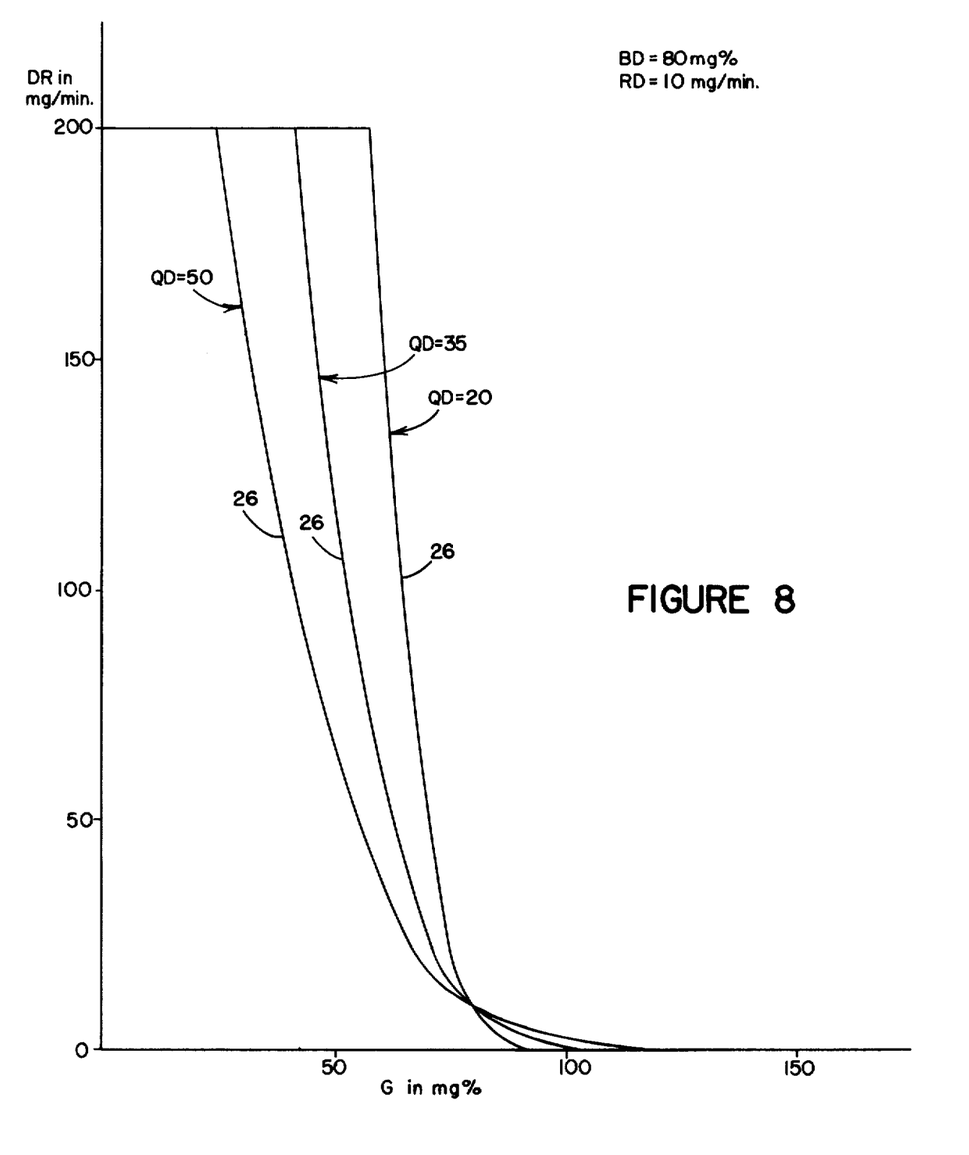
FIG. 8 is a family of curves showing operation of the apparatus of the present invention for glucose infusion vs. blood glucose concentration for several values of QD.

Typical operating conditions for computer calculated glucose infusion rates (DR) vs. measured serial blood glucose concentrations (G) are shown in FIG. 8. The BD and RD are kept constant at typical values of 80 mg. percent and 10 mg. per min., respectively. QD is shown for three typical values of 20, 35 and 50 mg. percent. The calculated DR is then obtained for the appropriate curve 26 depending on the measured blood glucose reading (G) and the appropriate QD selected by the operator. Comparable curves can also be obtained for different values of QD.

When glucose is being infused, the equation portion relating to (BD −G GD) +1 must have a value greater than zero. If this value is less than zero, the computer will stop all glucose infusion.

It can be seen from the above discussion that the apparatus of the present invention provides considerable flexibility to the operator to select not only the specific desired mode of operation but also to select desired control values in the computer operating equation for the selected operating mode. It is possible, when desired to have the apparatus simultaneously infusing both insulin and glucose according to separate different operating modes if this is necessary to maintain proper control over the blood glucose concentration of the patient. The operator can thus program the apparatus to most closely match the physiological condition of the particular patient and most effectively control the blood glucose concentration of this patient at a predetermined level.

The apparatus of the present invention has been used in conjunction with several diabetic patients and has successfully maintained their blood glucose concentrations at desired levels under both stressed and unstressed situations and with various diets. The degree of control achieved has been superior to that obtained by prior art apparatus.

In the apparatus of FIG. 1, any suitable sensor means can be employed to measure the blood glucose concentration of the blood samples obtained from the patient. Likewise any suitable pump can be used to infuse insulin or glucose to the patient in response to signals from the computer. The particular details of the sensor 11, the computer 12 or the pump 13 do not form a part of the present invention. It is understood that for convenience there will be separate pumps for infusion of insulin and for infusion of glucose.

What is claimed is:

1. Apparatus for controlling the concentration of glucose in the blood stream of a subject by controlled supply of insulin to such subject dependent upon both the particular concentration of glucose in said blood stream and the rate of change of said blood glucose concentration comprising means for determining serial values of blood glucose concentration and for providing computer input signals corresponding to said serial values; computer means coupled to receive said serial input signals, said computer means being programmed to provide output signals based upon said serial input signals; and pump means responsive to said output signals for supplying insulin to such subject at a rate determined by said output signals; said computer being capable of deriving output signals from serial input signals in accordance with an equation of the form $$IR = RI \left( \frac{G + GD - BI}{QI} + 1 \right)^4$$

wherein

IR = calculated insulin infusion rate $BI$ = basal glucose concentration
$RI$ = desired basal insulin infusion rate at BI
$G$ = measured previous serial blood glucose reading
and $BI$, $RI$, and $QI$ are preselected values and wherein if the blood glucose concentration is rising $$GD = (K_R A^2 10) + 6A$$

wherein $A$ is the average change in blood gulcose concentration over several previous serial readings and $K_R$ is a preselected value and wherein if the blood glucose concentration is falling $$GD = (K_F A^2 10) + 6A$$

wherein $A$ is the same as above and $K_F$ is a preselected value which is different from and less than $K_R$, said GD being substracted from $G$ in the above equation when the blood glucose concentration is falling.

2. Apparatus for controlling the concentration of glucose in the blood stream of a subject by controlled supply of insulin to such subject dependent upon the particualr concentration of glucose in said blood stream comprising means for determining serial values of blood glucose concentration and for providing computer input signals corresponding to said serial values; computer means coupled to receive said serial input signals, said computer means being programmed to provide output signals based upon said serial input signals; and pump means responsive to said output signals for supplying insulin to such subject at a rate determined by said output signals; said computer being capable of deriving output signals from serial input signals in accordance with an equation of the form $$IR = RI \left( \frac{G - BI}{QI} + 1 \right)^4$$

wherein
$IR$ = calculated insulin infusion rate
$BI$ = basal glucose concentration
$RI$ = desired basal insulin infusion rate at $BI$
$G$ = measured previous glucose reading and $BI$, $RI$ and $QI$ are preselected values.

3. Apparatus for controlling the concentration of glucose in the blood stream of a subject by controlled supply of insulin to such subject dependent upon the rate of change of glucose concentration in said blood stream comprising means for determining serial values of blood glucose concentration and for providing computer input signals corresponding to said serial values; computer means coupled to receive said serial input signals, said computer means being programmed to provide output signals based upon said serial input signals; and pump means responsive to said output signals for supplying insulin to such subject at a rate determined by said output signals; said computer being capable of deriving output signals from serial input signals in accordance with an equation of the form $$IR = RI \left( \frac{G + GD - BI}{QI} + 1 \right)^4 - RI \left( \frac{G - BI}{QI} + 1 \right)^4$$

wherein
$IR$ = calculated insulin infusion rate
$BI$ = basal glucose concentration
$RI$ = desired basal insulin infusion rate at $BI$
$G$ = measured previous glucose reading and $BI$, $RI$ and $QI$ are preselected values and wherein if the blood glucose concentration is rising $$GD = (K_R A^2 10) = 6A$$

wherein $A$ = the average change in blood concentration over several previous serial readings and $K_R$ is a preselected value and wherein if the blood glucose concentration is falling $$GD = (K_F A^2 10) = 6A$$

wherein $A$ is the same as above and $K_F$ is a preselected value which is different from and less than $K_R$, said GD being substracted from $G$ in the above equation when the blood glucose concentration is falling.

4. Apparatus for controlling the concentration of glucose in the blood stream of a subject by controlled supply of glucose to such subject dependent upon the particular concentration of glucose in said blood stream comprising means for determining serial values of blood glucose concentration and for providing computer input signals corresponding to said serial values; computer means coupled to receive said serial input signals, said computer means being programmed to provide output signals based upon said serial input signals; and pump means responsive to said output signals for supplying glucose to such subject at a rate determined by said output signals; said computer being capable of deriving output signals from serial input signals in accordance with an equation of the form $$DR = RD \left( \frac{BD - G}{QD} + 1 \right)^4$$

wherein
$DR$ = calculated glucose infusion rate
$BD$ = basal glucose concentration
$RD$ = desired basal glucose infusion rate at $BD$
$G$ = measured previous glucose reading and $BD$, $RD$ and $QD$ are preselected values.

* * * * *